(12) United States Patent
Igawa et al.

(10) Patent No.: US 12,110,457 B2
(45) Date of Patent: Oct. 8, 2024

(54) METHOD OF ESTIMATING SURFACE TENSION OF COAL INERT MATERIAL, METHOD OF ESTIMATING SURFACE TENSION OF COAL, AND METHOD OF PRODUCING COKE

(71) Applicant: JFE Steel Corporation, Tokyo (JP)

(72) Inventors: Daisuke Igawa, Tokyo (JP); Yusuke Dohi, Tokyo (JP); Tetsuya Yamamoto, Tokyo (JP)

(73) Assignee: JFE Steel Corporation, Tokyo (JP)

( * ) Notice: Subject to any disclaimer, the term of this patent is extended or adjusted under 35 U.S.C. 154(b) by 29 days.

(21) Appl. No.: 17/770,573

(22) PCT Filed: Oct. 14, 2020

(86) PCT No.: PCT/JP2020/038830
§ 371 (c)(1),
(2) Date: Apr. 20, 2022

(87) PCT Pub. No.: WO2021/085146
PCT Pub. Date: May 6, 2021

(65) Prior Publication Data
US 2022/0290054 A1   Sep. 15, 2022

(30) Foreign Application Priority Data
Oct. 28, 2019   (JP) .................. 2019-194865

(51) Int. Cl.
*C10B 57/04* (2006.01)
*C10L 5/04* (2006.01)
(Continued)

(52) U.S. Cl.
CPC ............. *C10B 57/04* (2013.01); *C10L 5/04* (2013.01); *G01N 13/00* (2013.01); *G01N 33/222* (2013.01)

(58) Field of Classification Search
CPC ........ C10B 45/00; C10B 57/04; G01N 13/00; G01N 33/222; C10L 5/04
See application file for complete search history.

(56) References Cited

U.S. PATENT DOCUMENTS 4,135,983 A * 1/1979 Kiritani .................. C10B 55/02
208/22
9,463,980 B2 * 10/2016 Fukada ................ G01N 33/222
(Continued)

FOREIGN PATENT DOCUMENTS

CN   104185783 A   12/2014
JP   S60-95354 A   5/1985
(Continued)

OTHER PUBLICATIONS

Office Action dated Feb. 10, 2022, of counterpart Taiwanese Patent Application No. 109136838, along with an English translation.
(Continued)

Primary Examiner — Jonathan Miller
(74) Attorney, Agent, or Firm — DLA Piper LLP (US)

(57) ABSTRACT

A method of estimating a surface tension of coal inert material includes determining in advance a first relational expression representing a relationship between a surface tension of coal inert material and a physical property value representing a coal rank; and measuring the physical property value representing the coal rank of a coal for which the surface tension of coal inert material is to be estimated, and calculating the surface tension of the coal inert material by using the measured physical property value representing the coal rank and the first relational expression.

8 Claims, 4 Drawing Sheets

(51) Int. Cl.
*G01N 13/00* (2006.01)
*G01N 33/22* (2006.01)

(56) References Cited

U.S. PATENT DOCUMENTS

| | | | |
|---|---|---|---|
| 9,850,441 B2* | 12/2017 | Fukada | G01N 33/222 |
| 10,144,891 B2* | 12/2018 | Shimoyama | C10B 57/04 |
| 2013/0255142 A1* | 10/2013 | Dohi | C10B 57/06 |
| | | | 44/550 |
| 2015/0039242 A1 | 2/2015 | Fukada et al. | |
| 2015/0040468 A1* | 2/2015 | Shimoyama | C10L 5/04 |
| | | | 44/620 |
| 2015/0047961 A1* | 2/2015 | Fukada | C10B 57/04 |
| | | | 201/1 |
| 2015/0075961 A1* | 3/2015 | Fukada | G01N 13/00 |
| | | | 44/620 |
| 2015/0075962 A1 | 3/2015 | Shimoyama et al. | |
| 2016/0084816 A1 | 3/2016 | Sumi et al. | |

FOREIGN PATENT DOCUMENTS

| | | |
|---|---|---|
| JP | 8-176553 A | 7/1996 |
| JP | 2000-356633 A | 12/2000 |
| JP | 2005-194358 A | 7/2005 |
| JP | 2005-281355 A | 10/2005 |
| JP | 2007-132795 A | 5/2007 |
| JP | 2011-213827 A | 10/2011 |
| JP | 2014-202711 A | 10/2014 |
| JP | 2014-218648 A | 11/2014 |
| JP | 5737473 B2 | 6/2015 |
| JP | 2015-193829 A | 11/2015 |
| JP | 2016-69469 A | 5/2016 |
| JP | 2018-197319 A | 12/2018 |
| JP | 2019-31641 A | 2/2019 |
| RU | 2640183 C2 | 12/2017 |
| TW | 201319239 A | 5/2013 |
| WO | 2013/145677 A1 | 10/2013 |
| WO | 2013/145678 A1 | 10/2013 |
| WO | 2013/145679 A1 | 10/2013 |
| WO | 2014/129337 A | 8/2014 |

OTHER PUBLICATIONS

Extended European Search Report dated Nov. 15, 2022, of counterpart European Patent Application No. 20882743.6.
Office Action dated Nov. 16, 2022, of counterpart Russian Patent Application No. 2022110743, along with an English translation.
M. Nagayama et al., "Evaluation of Coal Compatibility Effect in Coke Strength by Surface Tension of Semi-coke," ISIJ International, vol. 57, No. 6, pp. 989-995, Jan. 1, 2017.
M.A. Duchesne et al., "Slag Density and Surface Tension Measurements by the Constrained Sessile Drop Method," Article in "Fuel," vol. 188, pp. 173-181, 2017.
Office Action dated Sep. 14, 2023, of counterpart Chinese Patent Application No. 202080072507.1, along with a Concise Statement of Office Action in English.
International Search Report dated Dec. 15, 2020, of corresponding International Application No. PCT/JP2020/038830, along with an English translation.
Williams, M.C. & Fuerstenau, D.W., "A simple flotation method for rapidly assessing the hydrophobicity of coal particles," *International Journal of Mineral Processing,* vol. 20, Issues 1-2, 1987, pp. 153-157, (Partial).
Office Action dated Sep. 28, 2023, of counterpart Canadian Patent Application No. 3,152,872.
Official Action dated Dec. 15, 2023, of related U.S. Appl. No. 17/770,354.
Request for Submission of Opinion dated Jan. 15, 2024, of counterpart Korean Patent Application No. 10-2022-7012969, along with a Concise Statement of Relevance of Office Action in English.
Official Action dated Mar. 5, 2024, of related U.S. Appl. No. 17/770,354.
Office Action dated Aug. 2, 2024, of counterpart Canadian Patent Application No. 3,152,872.

* cited by examiner

METHOD OF ESTIMATING SURFACE TENSION OF COAL INERT MATERIAL, METHOD OF ESTIMATING SURFACE TENSION OF COAL, AND METHOD OF PRODUCING COKE

TECHNICAL FIELD

This disclosure relates to a method of estimating the surface tension of coal inert material, a method of estimating the surface tension of coal, and a method of producing coke.

BACKGROUND

Coke used as a blast furnace raw material for pig iron production in blast furnaces preferably has high strength. This is because coke having low strength degrades in blast furnaces and thus inhibits gas permeability in blast furnaces, which hinders stable production of pig iron.

Coke is produced by carbonizing coal. Carbonization is a process of heating coal at a pyrolysis temperature or higher (about 300° C. or higher) in a non-oxidizing atmosphere. Coal that softens and melts at 350° C. to 600° C. in a carbonization process is preferably used as a raw material of coke. When softening and melting, coal powder or particles adhere to and fuse with each other to form lump coke.

To produce coke having high strength, coal particles preferably adhere well to each other. The surface tension of heat-treated coal (semicoke) is used as a physical property value to evaluate the adhesiveness of the coal.

Examples of the method of measuring the surface tension of materials such as coal include a capillary-rise method, a maximum bubble pressure method, a drop weight method, a pendant drop method, a ring method, a Wilhelmy method, an advancing/receding contact angle method, a tilting plate method, and a film flotation method. Since coal is composed of various molecular structures and thus expected to have uneven surface tension, the film flotation method in D. W. Fuerstenau: International Journal of Mineral Processing, 20 (1987), 153 or Japanese Patent No. 5737473 expected to evaluate the surface tension distribution is said to be the most reasonable measurement method.

The film flotation method is a technique based on the idea that pulverized sample particles placed in liquid and starting to sink from a floating state have the same surface tension as the liquid. Sample particles are dropped into liquids having various surface tensions, and the mass ratio of sample particles that float in each liquid is determined. The surface tension distribution is obtained from the result. The film flotation method can measure the surface tension of any coal, regardless of the type of coal such as hard coking coal, non- or slightly caking coal, anthracite, and heat-treated coal (semicoke) made by treating such coal with heat.

The film flotation method has a problem of taking a long time (about one day) to measure the surface tension of coal and is not effective in terms of time. The film flotation method also has a problem of a complicated process of measuring the surface tension, and only skilled measurers can stably measure the surface tension. It could therefore be helpful to provide a method of easily estimating the surface tension of coal.

SUMMARY

We thus provide:
(1) A method of estimating a surface tension of coal inert material includes: determining in advance a first relational expression representing a relationship between a surface tension of coal inert material and a physical property value representing a coal rank; and measuring the physical property value representing the coal rank of a coal for which the surface tension of coal inert material is to be estimated, and calculating the surface tension of the coal inert material by using the measured physical property value representing the coal rank and the first relational expression.

(2) In the method of estimating a surface tension of coal inert material according to (1), the physical property value representing the coal rank is a mean maximum vitrinite reflectance.

(3) In the method of estimating a surface tension of coal inert material according to (1), the surface tension is a surface tension of coal inert material of a semicoke made by heating coal to a temperature of 350° C. or higher and 800° C. or lower.

(4) A method of estimating a surface tension of coal includes: calculating a second relational expression representing a relationship between a surface tension and a total inert content of coal from a predetermined surface tension of reactives and a surface tension of inert material estimated by the method of estimating a surface tension of coal inert material according to any one of (1) to (3); and measuring the total inert content of a coal of which the surface tension is to be estimated, and calculating the surface tension of the coal by using the measured total inert content and the second relational expression.

(5) In the method of estimating a surface tension of coal according to (4), the predetermined surface tension of reactives is an arithmetic mean of surface tensions of reactives in different brands of coal.

(6) A method of producing coke includes blending coals having surface tensions estimated by the method of estimating a surface tension of coal according to (4) or (5) to form a coal blend, and carbonizing the coal blend to produce coke.

The surface tension of inert material can be easily estimated by carrying out the method of estimating the surface tension of coal inert material, and the surface tension of coal can be easily estimated by using the surface tension of the inert material. When the surface tension of coal can easily be estimated in this way, the estimated value of the surface tension can be used to investigate blending of coals, which enables production of coke with high quality.

DETAILED DESCRIPTION

Figure 1:
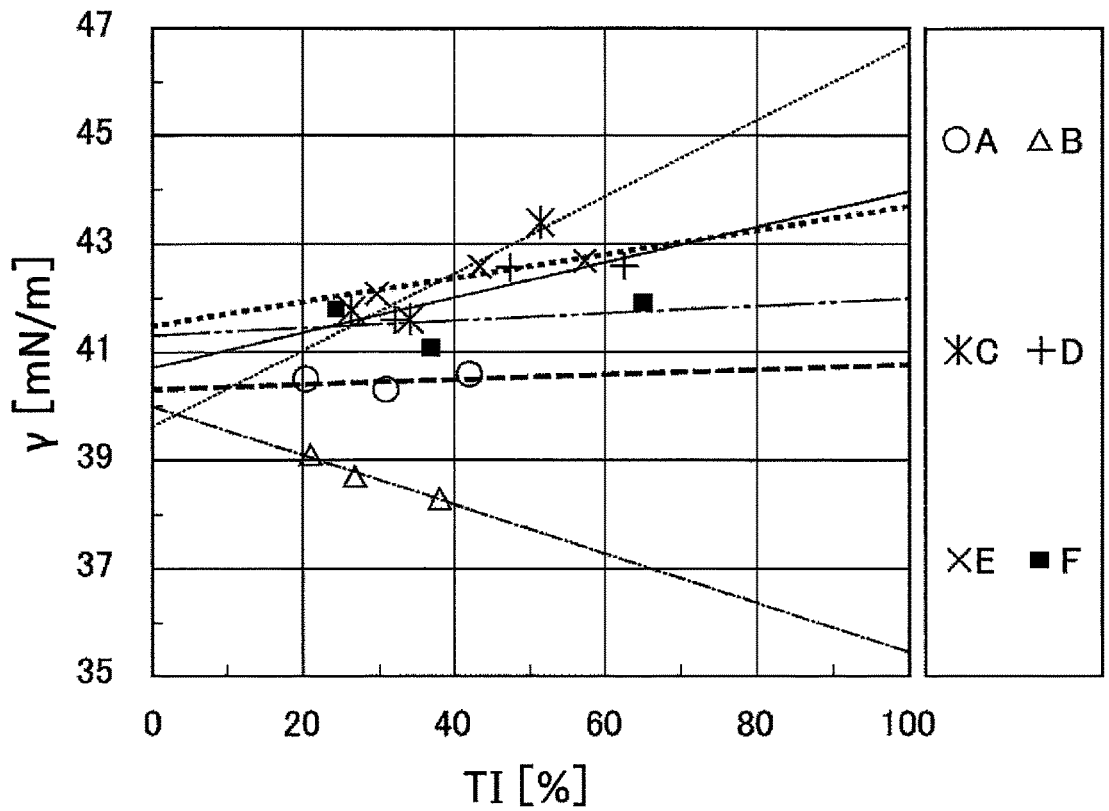
FIG. 1 is a graph showing plots (3 points) of the surface tension of samples having different inert contents and the regression line of the plots for each of samples having different inert contents in 6 brands (A to F) of coal.

Our methods will be described below through examples. The following description mainly focuses on examples of the method of estimating the surface tension of coal. The method of estimating the surface tension of coal inert material and the method of producing coke will be described in the examples.

We focus on coal components that soften and melt with heat (hereinafter reactives) and coal components that neither soften nor melt with heat (hereinafter inert material). First, the relationship between the surface tensions of the reactives and the inert material and the surface tension of coal will be described. In the following description, the surface tension of coal may be referred to as $\gamma$. Since coal inert material is harder than reactives, the inert material tends to concentrate in coarse particles of coal after pulverizing. This tendency is used to prepare samples having different inert contents from the same brand of coal by pulverizing and sifting. The total inert content (hereinafter TI) of each of the samples having different inert contents prepared in this way is measured, and the samples are each treated with heat at a predetermined temperature to form semicokes. The TI is the total inert content defined in JIS M 8816 and indicates the proportion (vol %) of inert material contained in coal.

In this example, the coal of which the surface tension is to be estimated includes heat-treated coal, that is, semicoke. The method of estimating the surface tension of coal according to this example can be applied to coal without a heat treatment as well as semicoke. Since the surface tension of semicoke is particularly useful for predicting coke strength and producing coke with high strength, the method of measuring the surface tension of semicoke, which is heat-treated coal, will be described in this example. The semicoke is produced in the following (a) to (c).

(a) Pulverizing coal. With regard to the size of particles of pulverized coal, the coal is preferably pulverized to a particle size of 250 μm or less, more preferably pulverized to 200 μm or less, which is the size of particles in proximate analysis of coal described in JIS M8812 to prepare uniform samples from coal which is not uniform in macerals and properties.

(b) Heating the pulverized coal to a temperature of 350° C. or higher and 800° C. or lower at an appropriate heating rate with no air or in an inert gas. The heating rate is preferably set according to the heating rate during production of coke in a coke oven.

(c) Cooling the heated coal in an inert gas to produce semicoke.

With regard to the heating temperature for heating the coal, the coal is preferably heated to a temperature between 350° C. at which the coal starts to soften and melt and 800° C. at which coking is complete, based on the idea that the surface tension has an effect on adhesion between coal particles. However, in a range of heating temperatures of 350° C. to 800° C., the temperature that particularly contributes to adhesion is 350° C. to 550° C. which is a temperature of softening and melting, and the adhesion structure may be set around 500° C. For this, the heating temperature is particularly preferably 480° C. to 520° C., which is around 500° C., and the heating temperature is set to 500° C. in this example. Heating is preferably performed in an inert gas (e.g., nitrogen, argon, helium) atmosphere, which is unreactive with coal.

Cooling is preferably performed in an inert gas atmosphere, which is unreactive with coal. The heat-treated coal is preferably rapidly cooled at a cooling rate of 10° C./sec or more. The reason for the rapid cooling is to maintain a molecular structure in the reactive state, and the cooling rate is preferably 10° C./sec or higher at which the molecular structure may not change. The rapid cooling may be performed by using liquid nitrogen, iced water, water, or an inert gas such as a nitrogen gas. The rapid cooling is preferably performed by using liquid nitrogen.

The surface tension of the coal can be measured by using the film flotation method described in D. W. Fuerstenau: International Journal of Mineral Processing, 20 (1987), 153. That method can be used for both coal and semicoke made from the coal, and the surface tension distribution can be obtained by using a finely pulverized sample. The mean of the obtained surface tension distribution is defined as a surface tension (hereinafter $\gamma$) of the sample. The measurement of the surface tension of semicoke using the film flotation method is specifically described in Japanese Patent No. 5737473.

FIG. 1 is a graph showing plots (3 points) of the surface tension (mean of surface tension distribution) of samples having different inert contents and the regression line of the plots for each of 6 brands (A to F) of coal treated with heat at 500° C. (semicokes). In FIG. 1, the horizontal axis represents TI (%), and the vertical axis represents $\gamma$ (mN/m). Table 1 shows the properties of the coals A to F.

TABLE 1

| Brand | logMF (log/ddpm) | Ro (%) | TI (%) | $\gamma$ (mN/m) | $\gamma_0$ (mN/m) | $\gamma_{100}$ (mN/m) |
|---|---|---|---|---|---|---|
| A | 2.97 | 1.20 | 20.36 | 40.5 | 40.3 | 40.8 |
| B | 0.48 | 1.56 | 20.96 | 39.1 | 40.0 | 35.5 |
| C | 2.94 | 0.97 | 33.98 | 41.6 | 39.6 | 46.7 |
| D | 2.78 | 0.98 | 47.39 | 42.6 | 40.7 | 44.0 |
| E | 2.77 | 0.97 | 43.40 | 42.6 | 41.5 | 43.7 |
| F | 1.34 | 1.30 | 36.88 | 41.1 | 41.3 | 42.0 |

Each regression line in FIG. 1 is a simple regression equation of $\gamma$ against TI and calculated by using the least squares method to minimize the error between the simple regression equation and each plot in each coal. As shown in FIG. 1, the plots of each coal are on the regression line, and an approximately linear relationship is observed between TI and $\gamma$. For this, a value corresponding to TI=100 on the regression line is the surface tension of inert material at 100% inert material (hereinafter $\gamma_{100}$), and a value corresponding to TI=0 is the surface tension at 100% reactives (hereinafter $\gamma_0$). When the reactives constitute 100% of coal, the inert material constitutes 0% of coal.

In Table 1, "log MF (log/ddpm)" is a common logarithmic value of the maximum fluidity (MF/ddpm) of coals measured by the Gieseler plastometer method described in JIS M8801. In Table 1, "Ro (%)" is a physical property value used in this example as an example measure of coal rank and is a mean maximum vitrinite reflectance in JIS M 8816. In Table 1, "TI (%)" is a total inert content (vol %) and calculated in accordance with Methods of microscopical measurement for the macerals for coal and coal blend in JIS M 8816 and formula (1) based on the Parr formula described in explanation of the Methods.

Inert content (vol %)=fusinite (vol %)+micrinite (vol %)+(2/3)×semifusinite (vol %)+mineral matter (vol %)  (1)

In Table 1, "γ (mN/m)" is the surface tension (mean of surface tension distribution) of semicokes made by treating coals A to F, which have been pulverized to a predetermined particle size, with heat at 500° C. in accordance with the film flotation method. "$\gamma_0$" is a value corresponding to TI=0 on the regression line of each of coals A to F shown in FIG. 1, and "$\gamma_{100}$" is a value corresponding to TI=100.

FIG. 1 shows that $\gamma_0$ has a tendency of convergence to a substantially constant value, regardless of the brand of coal. However, $\gamma_{100}$ does not have a tendency of convergence to a constant value and greatly varies according to the brand of coal. Since $\gamma_0$ has a tendency of convergence to a substantially constant value, the representative value of $\gamma_0$ can be predetermined from $\gamma_0$ calculated for different brands of coal. In this example, the representative value of $\gamma_0$ is defined as an arithmetic mean of $\gamma_0$ of different brands of coal.

Figure 2:
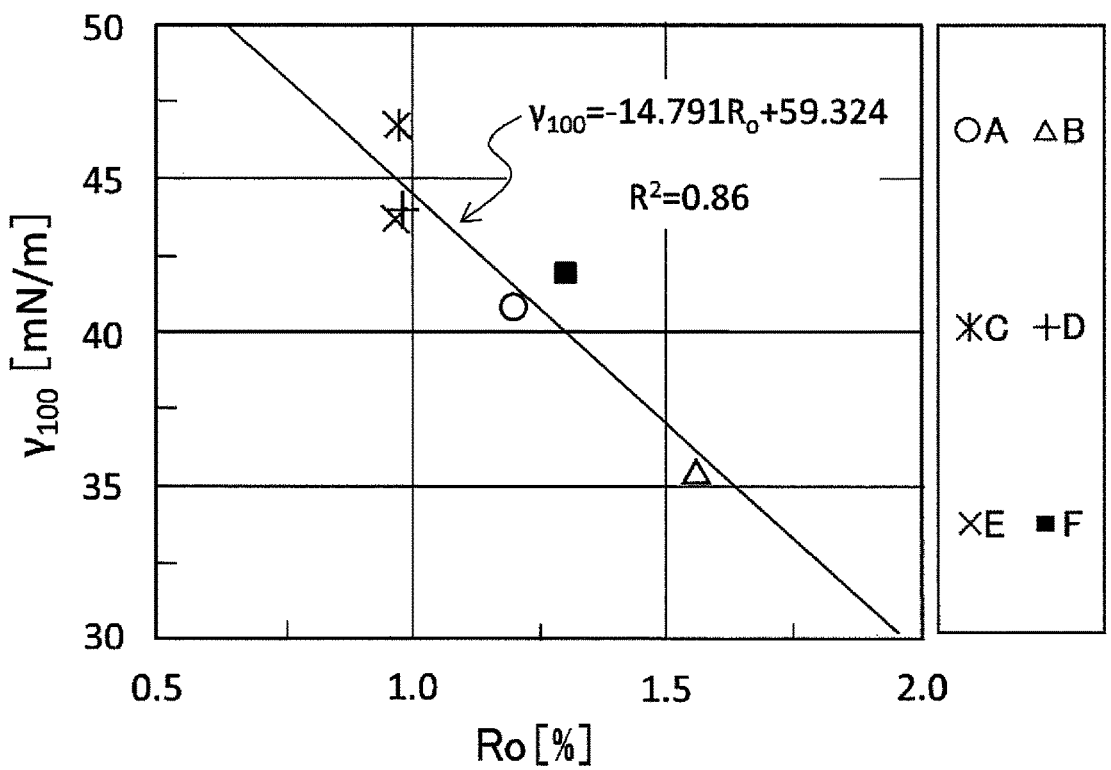
FIG. 2 is a graph showing the relationship between $\gamma_{100}$ and the mean maximum vitrinite reflectance of coal.

Since $\gamma_{100}$ greatly varies according to the brand of coal, it is necessary to determine $\gamma_{100}$ for each brand of coal. We found a good correlation between $\gamma_{100}$ and coal rank. FIG. 2 is a graph showing the relationship between $\gamma_{100}$ and the mean maximum vitrinite reflectance (hereinafter Ro) of coal. In FIG. 2, the horizontal axis represents Ro (%), and the vertical axis represents $\gamma_{100}$ (mN/m). The method of estimating the surface tension of coal inert material will be described with reference to FIG. 2. Each regression line in FIG. 2 is a simple regression equation of $\gamma_{100}$ against Ro and calculated by using the least squares method to minimize the error between the simple regression equation and each plot. This simple regression equation is the first relational expression representing the relationship between $\gamma_{100}$ and Ro, and the first relational expression is established by using coals A to F shown in Table 1 to obtain formula (2).

$$\gamma_{100} = -14.791 Ro + 59.324 \quad (2)$$

Table 2 shows the properties of coal G, which is not used to establish the first relational expression. Table 3 shows $\gamma_{100}$ calculated by using Ro shown in Table 1 and formula (2).

TABLE 2

| Brand | logMF (log/ddpm) | Ro (%) | TI (%) | γ (mN/m) | $\gamma_0$ (mN/m) | $\gamma_{100}$ (mN/m) |
|---|---|---|---|---|---|---|
| G | 1.67 | 1.23 | 22.10 | 40.2 | 39.5 | 41.2 |

TABLE 3

| Brand | $\gamma_{100}$ (Estimated Value) (mN/m) |
|---|---|
| A | 41.6 |
| B | 36.3 |
| C | 45.0 |
| D | 44.8 |
| E | 45.0 |
| F | 40.1 |
| G | 41.1 |

As shown in Table 3, $\gamma_{100}$ of coal G, which is not used to establish formula (2), is calculated by using Ro shown in Table 2 and formula (2) and found to be 41.1 mN/m. γ of each of semicokes made by treating three samples having different inert contents with heat at 500° C. is measured, and $\gamma_{100}$ calculated from the simple regression equation of γ is 41.2 mN/m. This result indicates that $\gamma_{100}$ can be accurately estimated from Ro by using formula (2), which is the first relational expression. The simple regression equation in FIG. 2 has a coefficient of determination $R^2$ of 0.86, which is close to 1. The coefficient of determination $R^2$ is a measure of the degree of correlation in the regression equation. The closer the coefficient of determination $R^2$ is to 1, the higher the degree of correlation between Ro and $\gamma_{100}$. This result indicates that $\gamma_{100}$ can be accurately estimated from the first relational expression and Ro. As described above, the method of estimating the surface tension of coal inert material includes determining in advance the first relational expression representing the relationship between $\gamma_{100}$ and Ro, measuring Ro of a coal of which $\gamma_{100}$ is to be estimated, and calculating the surface tension of inert material in the coal by using the measured Ro and the first relational expression.

To obtain $\gamma_{100}$ as described above, it is necessary to prepare two or more samples having different inert contents, measure the surface tension of each of the samples using the film flotation method after converting the samples into semicoke, and determine the simple regression equation of the surface tension. On the other hand, when the first relational expression representing the relationship between $\gamma_{100}$ and Ro is determined in advance as shown in FIG. 2, $\gamma_{100}$ can be calculated, only by measuring Ro of a target of which $\gamma_{100}$ is to be estimated, from the first relational expression and the measured Ro. Thus, it is understood that $\gamma_{100}$ can be easily estimated by using the method of estimating the surface tension of coal inert material.

As long as $\gamma_{100}$ can be estimated by using the method of estimating the surface tension of coal inert material, the relational expression representing the relationship between γ and TI corresponding to the simple regression equation shown in FIG. 1 can be calculated by using a predetermined representative value of $\gamma_0$ and the estimated $\gamma_{100}$. This relational expression is the second relational expression representing the relationship between γ and TI. The second relational expression can be represented by formula (3).

$$\gamma = [(\gamma_{100} - \gamma_0)/100] \times TI + \gamma_0 \quad (3)$$

The method of estimating the surface tension of coal according to this example includes determining in advance the second relational expression calculated from predetermined $\gamma_0$ and $\gamma_{100}$, measuring the TI of a coal of which γ is to be estimated, and calculating the surface tension of the coal from the measured value of TI and the second relational expression. The method of estimating the surface tension of coal according to this example uses, as $\gamma_0$, a predetermined representative value of $\gamma_0$ and uses, as $\gamma_{100}$, the estimated $\gamma_{100}$ calculated by using the method of estimating the surface tension of coal inert material. When the second relational expression is determined in advance, the surface tension of coal can be calculated, only by measuring TI of a coal of which the surface tension is to be estimated, from the second relational expression and the measured TI. The surface tension of the coal can thus be easily estimated by using the method of estimating the surface tension of coal according to this example.

Table 4 below shows $\gamma_0$ (representative value) and $\gamma_{100}$ (estimated value) used to determine the second relational expression and γ (estimated value) of coals A to F. γ (estimated value) is calculated by using the TI shown in Tables 1 or 2 and the second relational expression of each of coals A to F determined from $\gamma_0$ (typical value) and $\gamma_{100}$ (estimated value).

TABLE 4

| Brand | $\gamma_0$ (Representative Value) (mN/m) | $\gamma_{100}$ (Estimated Value) (mN/m) | $\gamma$ (Estimated Value) (mN/m) |
|---|---|---|---|
| A | 40.6 | 41.6 | 40.8 |
| B |  | 36.3 | 39.7 |
| C |  | 45.0 | 42.1 |
| D |  | 44.8 | 42.6 |
| E |  | 45.0 | 42.5 |
| F |  | 40.1 | 40.4 |
| G |  | 41.1 | 40.7 |

Figure 3:
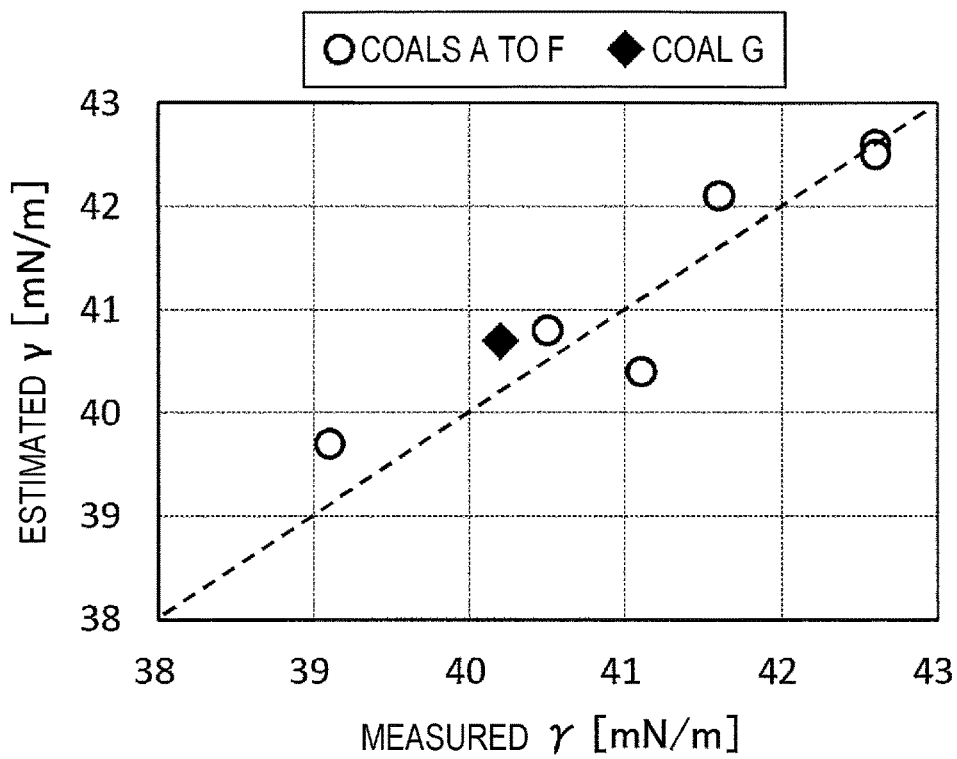
FIG. 3 is a graph showing the relationship between the measured surface tensions and the estimated surface tensions.

FIG. 3 is a graph showing the relationship between the measured surface tensions and the estimated surface tensions. In FIG. 3, the horizontal axis represents measured γ (mN/m), which is γ shown in Tables 1 or 2. The vertical axis represents estimated γ (mN/m), which is γ (estimated value) shown in Table 4. In FIG. 3, the circle plots represent coals A to F, and the solid square plots represent coal G. FIG. 3 indicates a very strong correlation between measured γ and estimated γ. This result demonstrates that γ can be accurately estimated by using the method of estimating the surface tension of coal according to this example.

FIGS. 2 and 3 show an example of estimating the surface tension of coals treated with heat at 500° C., but the heat treatment temperature of coals in this example is not limited to 500° C. To confirm that the method of estimating the surface tension of coal according to this example is not limited to heat treatment at 500° C., it is determined whether the relationship between TI and surface tension shown in FIG. 1 is also established at other heat treatment temperatures.

Samples having different TI contents are prepared by the above method using 3 brands (H, I, J) of coal. The samples are converted into semicokes according to the method including (a) to (c) described above under the same conditions except that only the heat treatment temperature is changed to 400° C. and 600° C. The surface tension of each semicoke is measured, and the relationship between TI and surface tension is determined in the same manner as in FIG. 1. Table 5 below shows the properties of the coals H to J.

TABLE 5

| Brand | logMF (log/ddpm) | Ro (%) | TI (%) |
|---|---|---|---|
| H | 0.85 | 1.51 | 41.04 |
| I | 0.95 | 1.32 | 43.86 |
| J | 1.83 | 1.02 | 50.25 |

Figure 4:
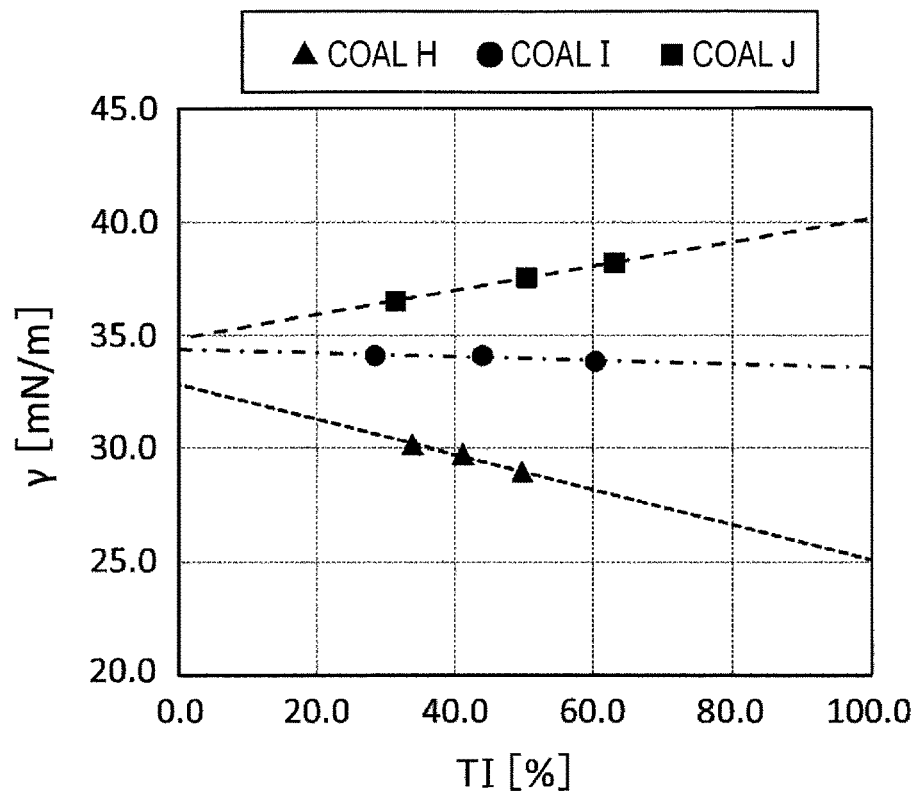
FIG. 4 is a graph showing plots (3 points) of the surface tension of samples having different inert contents and the regression line of the plots for each of 3 brands (H, I, J) of coal with a heat treatment temperature of 400° C.
Figure 5:
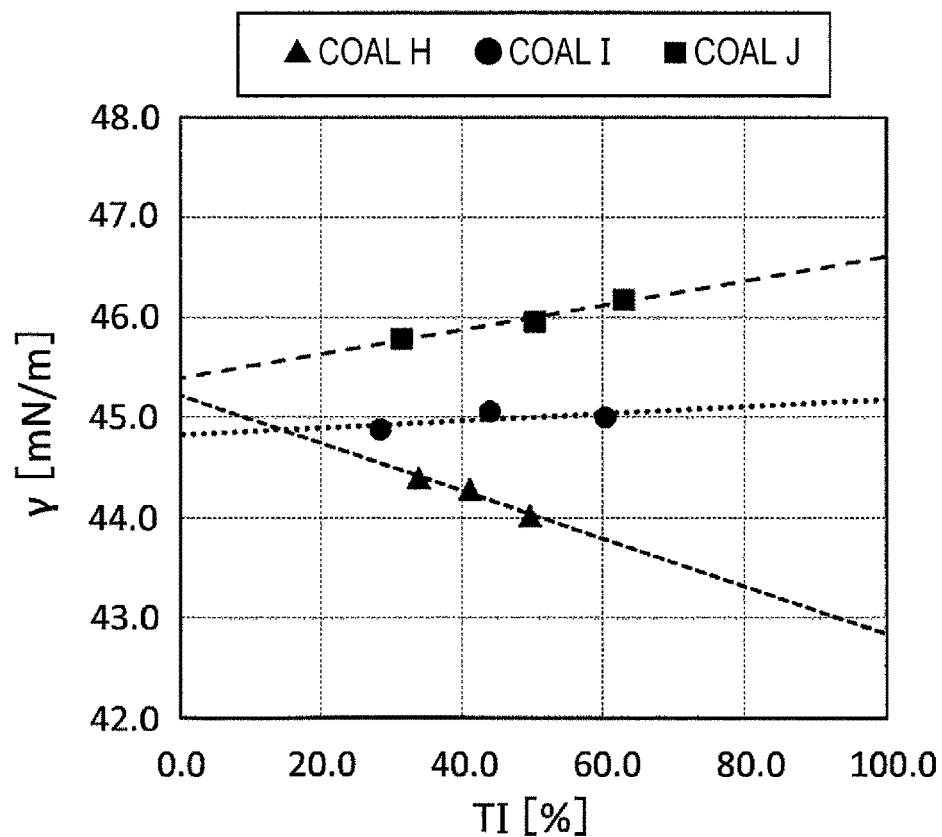
FIG. 5 is a graph showing plots (3 points) of the surface tension of samples having different inert contents and the regression line of the plots for each of 3 brands (H, I, J) of coal with a heat treatment temperature of 600° C.

FIG. 4 is a graph showing plots (3 points) of the surface tension of samples having different inert contents and the regression line of the plots for each of 3 brands (H, I, J) of coal with a heat treatment temperature of 400° C. FIG. 5 is a graph showing plots (3 points) of the surface tension of samples having different inert contents and the regression line of the plots for each of 3 brands (H, I, J) of coal with a heat treatment temperature of 600° C. In FIGS. 4 and 5, the horizontal axis represents TI (%), and the vertical axis represents γ (mN/m). As shown in FIGS. 4 and 5, a relationship similar to that in FIG. 1 is established between the TI and the surface tension of semicokes prepared at different heat treatment temperatures, and this tendency does not change for the same coal.

Figure 6:
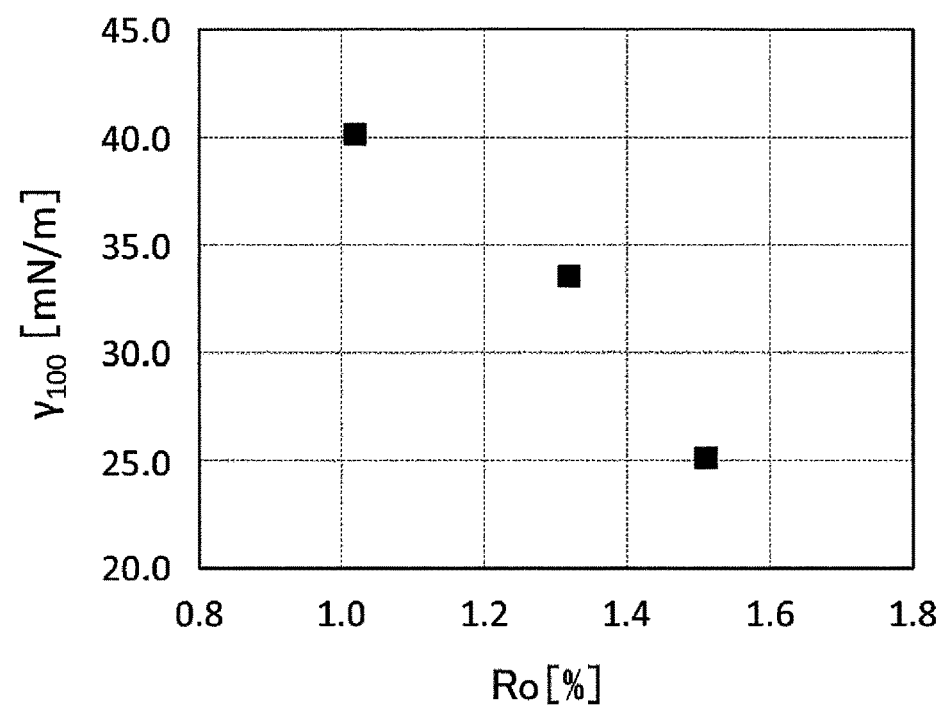
FIG. 6 is a graph showing the relationship between $\gamma_{100}$ and Ro of coals with a heat treatment temperature of 400° C.
Figure 7:
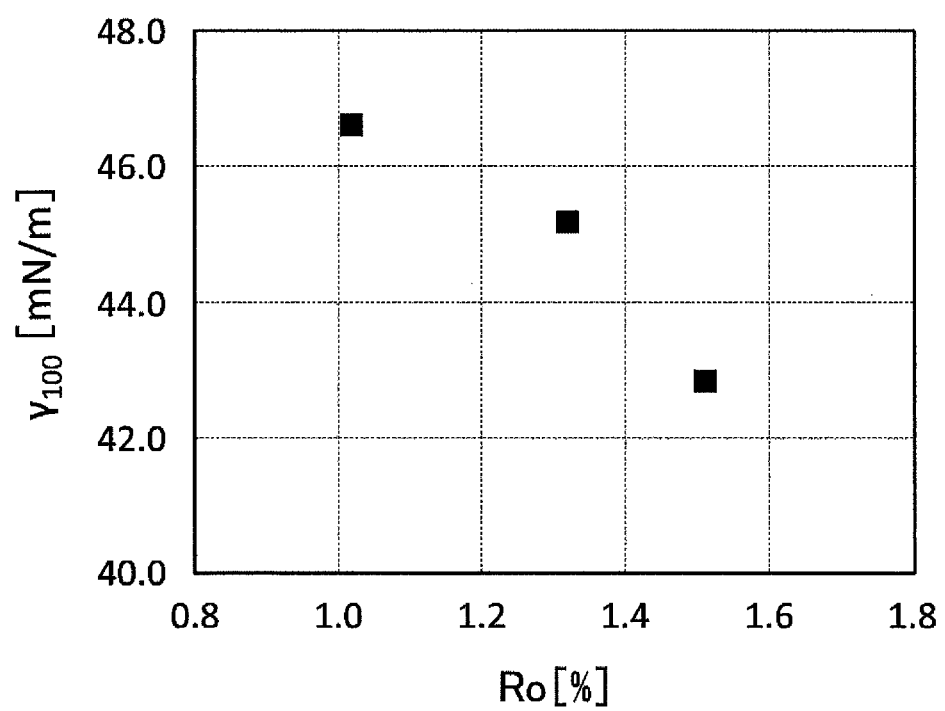
FIG. 7 is a graph showing the relationship between $\gamma_{100}$ and Ro of coals with a heat treatment temperature of 600° C.

In FIGS. 4 and 5, the regression line is obtained for each brand of coal and the surface tension $\gamma_{100}$ at TI=100% is obtained from the regression line. Then, the relationship between $\gamma_{100}$ and Ro of each coal is determined. FIG. 6 is a graph showing the relationship between $\gamma_{100}$ and Ro of coals with a heat treatment temperature of 400° C. FIG. 7 is a graph showing the relationship between $\gamma_{100}$ and Ro of coals with a heat treatment temperature of 600° C. In FIGS. 6 and 7, the horizontal axis represents Ro (%), and the vertical axis represents $\gamma_{100}$ (mN/m). As shown in FIGS. 6 and 7, a strong correlation is found between $\gamma_{100}$ and Ro as in FIG. 2 even when the heat treatment temperature is changed to 400° C. and 600° C.

This result indicates that the method of estimating the surface tension of coal according to this example can be used for semicokes prepared at different temperatures. Japanese Patent No. 5737473 also discloses that the surface tensions of semicokes prepared at heat treatment temperatures of 350° C. or higher and 800° C. or lower show the same tendency regardless of the type of coal. This indicates that the method of estimating the surface tension of coal according to this example can be used for semicokes prepared at a temperature of 350° C. or higher and 800° C. or lower as well as semicokes made by a heat treatment at 500° C.

In other words, estimation of the surface tension of inert material in a coal treated with heat at a predetermined temperature of 350° C. or higher and 800° C. or lower can be done by using the first relational expression representing the relationship between the surface tension of inert material in a semicoke made by a heat treatment at the predetermined temperature and the physical property value representing a coal rank. Accordingly, $\gamma_{100}$, which is the surface tension of inert material in a coal treated with heat at the predetermined temperature can be estimated.

Estimation of the surface tension of the coal treated with heat at a predetermined temperature of 350° C. or higher and 800° C. or lower can be done by using the second relational expression representing the relationship between the surface tension and the total inert content of the coal obtained from $\gamma_{100}$ of the coal estimated at the predetermined temperature and $\gamma_0$ at a predetermined temperature. The surface tension of the coal treated with heat at the predetermined temperature can be estimated accordingly.

The coals shown in Tables 1, 2, and 5 are examples of coal commonly used as a coke raw material. Coal used as a coke raw material has an MF of 0 to 60000 ddpm (log MF: 4.8 or less), a Ro of 0.6% to 1.8%, and a TI of 3 to 50 vol %. The method of estimating the surface tension of coal according to this example can be particularly preferably used for coals in such ranges.

In this example, Ro is used as a physical property value representing a coal rank. Other physical property values representing coal ranks include the volatile matter of coal, the carbon content, and the re-solidification temperature in softening and melting. These physical property values all show a good correlation with Ro. Therefore, the physical property value representing a coal rank may be a physical property value that correlates with the coal rank such as the volatile matter of coal, the carbon content, and the re-solidification temperature in softening and melting, instead of RO.

In general, coal maceral analysis regarding TI, physical property values representing coal ranks such as Ro, and other parameters is widely used in business transactions for the purpose of expressing the characteristics of coal, and these parameters are analyzed. Therefore, as long as $\gamma_{100}$ can be estimated from the coal rank such as Ro, and the surface tension of coal can be estimated by using the $\gamma_{100}$, the surface tension of coal can be estimated without relying on skilled measurers, and the time for measuring the surface tension can be saved.

The strength of a coke made from a coal blend containing a mixture of coals with similar γ is higher than that of a coke made from a coal blend containing a mixture of coals with different γ. If γ can be easily estimated by using the method of estimating the surface tension of coal according to this example, the estimated γ can be used to investigate blending of coals. The use of a coal blend having the blending ratio set by the blending investigation to produce coke thus enables production of coke with high quality.

The invention claimed is:

1. A method of estimating a surface tension of coal inert material comprising:
   determining in advance a first relational expression representing a relationship between a surface tension of coal inert material and a physical property value representing a coal rank;
   measuring the physical property value representing the coal rank of a coal for which the surface tension of coal inert material is to be estimated, and calculating the surface tension of the coal inert material by using the measured physical property value representing the coal rank and the first relational expression, and
   determining a blending ratio of different coals based on the calculated surface tension to form a coal blend;
   wherein the first relational expression is represented by formula (2):

$$\gamma_{100} = -14.791Ro + 59.324 \tag{2}$$

wherein, γ is the surface tension, $\gamma_{100}$ is the surface tension of inert material at 100% inert material and Ro is the physical property value representing coal rank and is a mean maximum vitrinite reflectance in JIS M 8816;
   wherein the resulting strength of the coke made from the coal blend containing a mixture of coals with a similar γ is higher than that of a coke made from a coal blend containing a mixture of coals with different γ.

2. The method according to claim 1, wherein the surface tension is a surface tension of coal inert material of a semicoke made by heating coal to a temperature of 350° C. or higher and 800° C. or lower.

3. A method of estimating a surface tension of coal comprising:
   calculating a second relational expression representing a relationship between a surface tension and a total inert content of coal from a predetermined surface tension of reactives and a surface tension of inert material estimated by the method according to claim 1; and
   measuring the total inert content of a coal of which the surface tension is to be estimated, and calculating the surface tension of the coal by using the measured total inert content and the second relational expression,
   wherein the second relational expression is represented by formula (3):

$$\gamma = [(\gamma_{100} - \gamma_0)/100] \times TI + \gamma_0 \tag{3}$$

wherein, γ is the surface tension,
   $\gamma_{100}$ is the surface tension of inert material at 100% inert material,
   $\gamma_0$ is the surface tension of inert material at 100% reactives, and
   TI is the total inert content defined in JIS M 8816 and indicates the proportion (vol %) of inert material contained in coal.

4. The method according to claim 3, wherein the predetermined surface tension of reactives is an arithmetic mean of surface tensions of reactives in different brands of coal.

5. A method of producing coke comprising: blending coals having surface tensions estimated by
   calculating a second relational expression representing a relationship between a surface tension and a total inert content of coal from a predetermined surface tension of reactives and a surface tension of inert material estimated by the method according to claim 1; and
   measuring the total inert content of a coal of which the surface tension is to be estimated, and calculating the surface tension of the coal by using the measured total inert content and the second relational expression,
   wherein the second relational expression is represented by formula (3):

$$\gamma = [(\gamma_{100} - \gamma_0)/100] \times TI + \gamma_0 \tag{3}$$

wherein, γ is the surface tension,
   $\gamma_{100}$ is the surface tension of inert material at 100% inert material,
   $\gamma_0$ is the surface tension of inert material at 100% reactives, and
   TI is the total inert content defined in JIS M 8816 and indicates the proportion (vol %) of inert material contained in coal
   to form a coal blend; and
   carbonizing the coal blend to produce coke.

6. A method of estimating a surface tension of coal comprising:
   calculating a second relational expression representing a relationship between a surface tension and a total inert content of coal from a predetermined surface tension of reactives and a surface tension of inert material estimated by the method according to claim 2; and
   measuring the total inert content of a coal of which the surface tension is to be estimated, and calculating the surface tension of the coal by using the measured total inert content and the second relational expression,
   wherein the second relational expression is represented by formula (3):

$$\gamma = [(\gamma_{100} - \gamma_0)/100] \times TI + \gamma_0 \tag{3}$$

wherein, γ is the surface tension,
   $\gamma_{100}$ is the surface tension of inert material at 100% inert material,
   $\gamma_0$ is the surface tension of inert material at 100% reactives, and
   TI is the total inert content defined in JIS M 8816 and indicates the proportion (vol %) of inert material contained in coal.

7. A method of producing coke comprising: blending coals having surface tensions estimated by
   calculating a second relational expression representing a relationship between a surface tension and a total inert content of coal from a predetermined surface tension of reactives and a surface tension of inert material estimated by the method according to claim 1; and
   measuring the total inert content of a coal of which the surface tension is to be estimated, and calculating the surface tension of the coal by using the measured total inert content and the second relational expression,
   wherein the second relational expression is represented by formula (3):

$$\gamma = [(\gamma_{100} - \gamma_0)/100] \times TI + \gamma_0 \tag{3}$$

wherein, γ is the surface tension, $\gamma_{100}$ is the surface tension of inert material at 100% inert material, $\gamma_0$ is the surface tension of inert material at 100% reactives, and TI is the total inert content defined in JIS M 8816 and indicates the proportion (vol %) of inert material contained in coal;

wherein the predetermined surface tension of reactives is an arithmetic mean of surface tensions of reactives in different brands of coal to form a coal blend; and carbonizing the coal blend to produce coke;

wherein the resulting strength of the coke made from the coal blend containing a mixture of coals with a similar γ is higher than that of a coke made from a coal blend containing a mixture of coals with different γ.

8. A method of producing coke comprising: blending coals having surface tensions estimated by determining in advance a first relational expression representing a relationship between a surface tension of coal inert material and a physical property value representing a coal rank;

measuring the physical property value representing the coal rank of a coal for which the surface tension of coal inert material is to be estimated, and calculating the surface tension of the coal inert material by using the measured physical property value representing the coal rank and the first relational expression, and determining a blending ratio of different coals based on the calculated surface tension to form a coal blend;

wherein the first relational expression is represented by formula (2);

$$\gamma_{100} = -14.791 Ro + 59.324 \quad (2)$$

wherein, γ is the surface tension, $\gamma_{100}$ is the surface tension of inert material at 100% inert material and Ro is the physical property value representing coal rank and is a mean maximum vitrinite reflectance in JIS M 8816 to form a coal blend; and carbonizing the coal blend to produce coke;

wherein the resulting strength of the coke made from the coal blend containing a mixture of coals with a similar γ is higher than that of a coke made from a coal blend containing a mixture of coals with different γ.

\* \* \* \* \*